(12) United States Patent
Thomas

(10) Patent No.: US 6,309,825 B1
(45) Date of Patent: Oct. 30, 2001

(54) ANALYTICAL AND THERAPEUTIC AGENTS

(75) Inventor: Siân Myra Thomas, Aylesbury (GB)

(73) Assignee: University of Leicester (GB)

(*) Notice: Subject to any disclaimer, the term of this patent is extended or adjusted under 35 U.S.C. 154(b) by 0 days.

(21) Appl. No.: 08/973,318

(22) PCT Filed: Feb. 5, 1996

(86) PCT No.: PCT/GB96/00220

§ 371 Date: Feb. 4, 1998

§ 102(e) Date: Feb. 4, 1998

(87) PCT Pub. No.: WO96/38588

PCT Pub. Date: Dec. 5, 1996

(30) Foreign Application Priority Data

May 31, 1995 (GB) .................................................. 9510954

(51) Int. Cl.$^7$ .............................. C12Q 1/68; G01N 33/53
(52) U.S. Cl. ................................................. 435/6; 435/7.5
(58) Field of Search .......................................... 435/6, 7.5

(56) References Cited

PUBLICATIONS

Musarrat, J and Wani, A.A. Quantitative immunoanalysis of promutagenic 8–hydroxy–2'–deoxyguanosine in oxidized DNA. Carcinogenesis. 15(9):2037–2043, 1994.*

Boorsma, D.M. Conjugation methods and biotin–avidin systems. In: Techniques in Immunocytochemistry, vol. 2. Academic Press, New York, pp. 155–174, 1983.*

"Assay of excised oxidative DNA lesions: Isolation of 8–oxoguanine and its nucleoside derivatives from biological fluids with a monoclonal antibody column," Porc. Natl. Acad. Sci., vol. 89., pp. 3375–3379, Apr. 1992.

* cited by examiner

Primary Examiner—David Saunders
Assistant Examiner—Mary Beth Tung
(74) Attorney, Agent, or Firm—Bracewell & Patterson LLP

(57) ABSTRACT

According to the present invention there is provided an agent and method of detecting 8-oxoquanine, 8-oxodeoxyguanosine, 8-oxoadenine, and 8-oxodeoxyadenosine.

14 Claims, 9 Drawing Sheets

ANALYTICAL AND THERAPEUTIC AGENTS

CROSS-REFERENCE TO RELATED APPLICATION

The present application claims priority to PCT/GB96/00220, titled "Analytical and Therapeutic Agents", having a priority date of May 31, 1995 and invented by Sian Myra Thomas.

BACKGROUND OF THE INVENTION

1. Field of the Invention

The present invention relates to agents for use in a method of detection of 8-oxoguanine, 8-oxodeoxyguanosine, 8-oxoadenine and 8-oxodeoxyadenosine, in particular for the detection of damaged nucleic acids, diagnostic tests for same and methods for the detection of same.

2. Description of the Related Art

Nucleic acid base damage, in particular oxidative base-damage of DNA, may arise as a result of a number of causes including toxins, carcinogenesis and neurodegenerative disorders. The detection of such damage is important in many fields of medicine including medical diagnostics, pathology and occupational health.

Present techniques for the detection of nucleic acid base damage rely on detection of 8-oxoguanine, a sensitive marker of DNA base-damage caused by oxygen free radicals (Kasai, H. and Nishimura, S., In: Sies, H., ed. Oxidative Stress: Oxidants and Antioxidants. London: Academic Press, 1991:99–116; Ames, B. N., 1989, Free Rad. Res. Comm., 7: 121–128), although 8-oxoguanine is only one of at least 20 products formed.

The use of 8-oxoguanine as a marker of oxidative damage to DNA followed the description of its analysis as the deoxynucleoside (8-oxodeoxyguanosine) in DNA digests by HPLC (high pressure liquid chromatography) with electrochemical detection (Floyd, R. A. et al., 1986, Free Rad. Res. Commun. 1: 163–172). Alternatively, gas chromatography-mass spectrometry (GC-MS) methods have been used to quantitate 8-oxoguanine as the free base (Dizdaroglu, M., 1994, Methods Enzymol., 234: 3–16), but the technique is expensive and technically demanding to use. Nevertheless the two techniques have been compared (as reviewed in Halliwell, B. and Dizdaroglu, M., 1992. Free Rad. Res. Commun. 16: 75–87) and results obtained do not concur. In general. levels of 8-oxoguanine are higher when determined by the GC-MS technique and even in freshly isolated cells, 2–11 fold higher values have been reported by GC-MS.

A number of other approaches to the determination of 8-oxoguanine in DNA have been described. $^{32}$P-postlabelling procedures are well established in the literature (Lu, L. J. W. et al., 1991, Chem. Pharmaceut. Bull. 39: 1880–1882; Povey, A. C. et al., In: Postlabelling Methods for Detection of DNA Adducts. Lyon, International Agency for Research on Cancer, 1993:105–114); these methods provide the potential for very sensitive detection although the techniques are very time-consuming and cumbersome. Capillary electrophoretic determinations of 8-oxodeoxyguanosine (Guarnieri C. et al., 1994, J. Chromatogr. B. 656: 209–213) and 8-oxoguanine (Poon, K. W. et al., 1995, Biochem. Soc. Trans. 23: 433s) have been described. To date, these techniques lack concentration sensitivity due to inherent lack of sensitivity of UV absorbence measurements.

SUMMARY OF THE INVENTION

According to the present invention there is provided an agent for use in a method of detection of 8-oxoguanine, 8-oxodeoxyguanosine, 8-oxoadenine and 8-oxodeoxyadenosine comprising a molecule which binds specifically to biotin and to at least one of 8-oxoguanine, 8-oxodeoxyguanosine, 8-oxoadenine and 8-oxodeoxyadenosine (the most common tautomeric forms thereof known as, respectively, 8-hydroxy guanine, 8-hydroxydeoxyguanosine, 8-hydroxyadenine and 8-hydroxydeoxyadenosine).

The purine base guanine bears little structural relation to the biotin molecule. However, although the exact nature of the binding of avidin to damaged DNA is currently unknown, the keto form of 8-oxoguanine, a damage product of oxidative DNA damage, has been found by the inventors to be structurally remarkably similar to biotin, and avidin, streptavidin and antibodies to biotin appear to have significant binding affinity for this oxidised base product.

Structural considerations strongly suggest that avidin will bind to 8-oxoadenine and 8-oxodeoxyadenosine since these compounds also possess the imidazilidone group.

By 'binds specifically' is meant that the agent has a specific affinity for a particular epitope or epitopes. Hence avidin binds specifically to at least biotin, 8-oxoguanine and 8-oxodeoxyguanosine, the molecules having the same or substantially similar epitopes. This specificity is analogous to an antibody specific to an epitope of a polypeptide also being specific to a mimotope (Geysen, H. M. et al., 1987, Journal of Immunological Methods, 102: 259–274) of the epitope, although the sequence of the mimotope may be different to that of the polypeptide.

The agent may have substantially the same binding specificity for biotin as avidin or streptavidin. It may also have substantially the same binding specificity for at least one of 8-oxoguanine, 8-oxodeoxyguanosine, 8-oxoadenine and 8-oxodeoxyadenosine as avidin or streptavidin.

By "the same binding specificity" is meant that the agent-for example a fragment, analogue, antibody or antigen binding fragment—is specific to substantially the same epitope or epitopes as avidin or streptavidin.

The agent may be selected from any one of the group of avidin and streptavidin.

The agent may comprise a fragment or an analogue of avidin or streptavidin. Avidin and streptavidin may be readily studied and altered to produce fragments of the molecule, for example fragments which comprise solely the biotin-binding part of the molecule. Analogues (to the molecules themselves or to fragments thereof) may also be produced. For example the analogues may have an altered binding specificity or binding affinity for the biotin molecule or for damaged DNA.

By "fragment or analogue of avidin or streptavidin" is meant a fragment or analogue of the avidin or streptavidin molecule which binds specifically to biotin and to at least one of 8-oxoguanine, 8-oxodeoxyguanosine, 8-oxoadenine and 8-oxodeoxyadenosine.

The present inventors have found that, remarkably, avidin, streptavidin and antibody specific to biotin may be used to detect 8-oxoguanine, 8-oxodeoxyguanosine, 8-oxoadenine and 8-oxodeoxyadenosine, and therefore damaged nucleic acids, in particular damaged DNA.

Avidin is a naturally occurring factor found in egg white, which has a remarkable affinity ($K_a = 10^{15}$ $M^{-1}$) for the vitamin biotin (Bayer, E. A. and Ichek, M., 1990, Methods in Enzymol., 184: 49–67), and the bacterial analogue streptavidin, from *Streptomyces avidinii*, has a substantially similar binding affinity and specificity.

The biotin molecule (Green, N. M., 1972, Adv. Protein Chem., 29: 85–131) is largely hydrophobic and consists of a ureido group and an imidazilidone ring. It would appear that the whole molecule interacts with the avidin binding site, avidin comprising a stable tetramer with two-fold symmetry and containing four biotin binding sites arranged in two clusters. Although a wide range of compounds that are analogues of small fragments of the biotin molecule will bind to avidin, the binding of avidin to biotin appears to be of relatively high specificity since related compounds do not bind significantly at the 10 mM level (Green, 1972, supra).

Avidin is widely employed in both research and technology primarily as a secondary means of detection and amplification. It is frequently used to detect biotin in immunoassays where a primary antibody is either directly biotinylated or is bound by a secondary biotinylated antibody. It is also used where a target molecule, such as a base, is chemically modified by biotinylation to aid in its visualisation.

Avidin is not currently used for the direct detection of biomolecules other than biotin.

Alternatively, the agent may comprise an antibody or antigen binding fragment thereof.

Any antibody referred to herein may be a whole antibody or an antigen binding fragment thereof and may in general belong to any immunoglobulin class. Thus, for example, it may be an IgM, IgG or IgA, antibody. The antibody or fragment may be of animal, for example, mammalian origin and may be for example of murine, rat or human origin. It may be a natural antibody or a fragment thereof, or, if desired, a recombinant antibody fragment, i.e. an antibody or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in, for example, European Patent Specification No 239400); (2) recombinant antibodies or fragments wherein non-Fv sequences have been substituted by non-Fv sequences from other, different antibodies (as described in, for example, European Patent Specification Nos 171469, 173494 and 194276); or (3) recombinant antibodies or fragments possessing substantially the structure of a natural immunoglobulin but wherein the hinge region has a different number of cysteine residues from that found in the natural immunoglobulin but wherein one or more cysteine residues in a surface pocket of the recombinant antibody or fragment is in the place of another amino acid residue present in the natural immunoglobulin (as described in, for example, International Patent Application Nos PCT/GB88/00730 and PCT/GB88/00729).

The antibody or antigen-binding fragment may be of polyclonal or monoclonal origin. It may be specific for a number of epitopes or it may be specific for one.

Antigen binding antibody fragments include, for example, fragments derived by proteolytic cleavage of a whole antibody, such as F(ab')2, Fab' or Fab fragments, or fragments obtained by recombinant DNA techniques, for example Fv fragments (as described, for example, in International Patent Application No PCT/GB88/00747).

The antibodies according to the invention may be prepared using well-known immunological techniques employing as antigen the epitope or epitopes (or a mimotope thereof) to which avidin or streptavidin are specific in order to generate an antibody or an antigen binding fragment having substantially the same binding specificity for biotin as avidin or streptavidin. Thus, for example, any suitable host may be injected with the epitope or with the epitope coupled to an adjuvant or with peptides representing the epitope and the serum collected to yield the desired polyclonal antibody after appropriate purification and/or concentration (for example by affinity chromatography using the immobilised stress protein as the affinity medium). Alternatively splenocytes or lymphocytes may be recovered from the bacterial protein-injected host and immortalised using for example the method of Kohler et al. (1976. Eur. J. Immunol., 6: 511), the resulting cells being segregated to obtain a single genetic line producing monoclonal antibodies. Antibody fragments may be produced using conventional techniques, for example, by enzymatic digestion with pepsin or papain. Where it is desired to produce recombinant antibodies according to the invention these may be produced using, for example, the methods described in European Patent Specification Nos 171469, 173494, 194276 and 239400.

Antibodies according to the invention may be labelled with a detectable label using conventional procedures and the invention extends to such labelled antibodies or antibody conjugates.

The antibody may comprise the monoclonal BN-34 antibody supplied by Sigma (F 4024).

Experiments have shown (see 'Experimental' section below) that such agents are capable of binding specifically to damaged nucleic acid bases.

The agent may bind to damaged nucleic acid bases. The agent may bind to oxidative base-damaged nucleic acids.

The agent may bind to damaged DNA bases. The agent may bind to damaged RNA bases.

The nucleic acid bases may be in the free base form or they may be bound to other molecules, e.g. to sugar-phosphate backbones to form DNA or RNA.

The oxidative base-damaged nucleic acids may be 8-oxoguanine, 8-oxodeoxyguanosine, 8-oxoadenine or 8-oxodeoxyadenosine.

The agent may bind to damaged bases of a single-stranded nucleic acid molecule. The agent may bind to damaged bases of a double-stranded nucleic acid molecule.

The agent may bind to damaged nuclear DNA bases. The agent may bind to damaged mitochondrial DNA. Mitochondrial DNA has been shown to possess limited repair and is considerably more susceptible to oxidative damage than nuclear DNA (Richter, C. et al., 1988, Proc. Natl. Acad. Sci. USA, 85: 6465–6467).

The agent may be used in a diagnostic test method for the detection of damaged nucleic acid bases, in particular DNA or RNA. Such a method may comprise a standard test method in which the binding of an agent to a target is detected and analysed, thereby determining whether damaged nucleic acid bases are present. For example, an agent (e.g. avidin) may be bound to a solid support and then exposed to a sample from a patient to be tested, effectively purifying any damaged nucleic acid bases from the sample. After a suitable time period the sample may be removed and the support-bound agent tested for the presence of damaged nucleic acid bases.

Such a diagnostic test method may comprise the steps of:
a) reacting the agent with a DNA- or RNA-containing sample;
b) detecting any binding reaction between the sample and the agent; and c) correlating detection of the sample-agent binding reaction with the existence and quantity of damaged DNA.

Alternatively, the agent may be simply used to purify 8-oxoguanine, 8-oxodeoxyguanosine, 8-oxoadenine or 8-oxodeoxyadenosine from a mixture (e.g. a reaction mixture). Such a purification may for example be used in the manufacture of 8-oxoguanine, 8-oxodeoxyguanosine, 8-oxoadenine or 8-oxodeoxyadenosine.

The agent may be used in a method of treatment or diagnosis of the human or animal body.

Also provided according to the present invention is a method for detecting nucleic acid base damage comprising the steps of:

a) reacting a nucleic acid base-containing sample with an agent comprising a molecule which binds specifically to biotin and to at least one of 8-oxoguanine, 8-oxodeoxyguanosine, 8-oxoadenine and 8-oxodeoxyadenosine;

b) detecting any binding reaction between the sample and the agent; and c) correlating detection of the sample-agent binding reaction with the existence and quantity of damaged nucleic acid bases.

The said molecule may bind to oxidative base-damaged nucleic acids. It may bind to said damaged DNA bases. It may bind to said damaged RNA bases.

The said molecule may bind to damaged nucleic acid bases of a single-stranded nucleic acid molecule. It may bind to damaged nucleic acid bases of a double-stranded nucleic acid molecule.

The damaged nucleic acid bases may be damaged nuclear DNA bases. They may be damaged mitochondrial DNA bases.

The method may be a method of treatment or diagnosis of the human or animal body.

In the testing of any sample, the sample may be free from contamination by biotin.

Potential diagnostic test uses include medical diagnostics, pathology and occupational health, and could comprise the screening of bodily fluids and biopsy specimens. Also included is toxicological screening for compounds with potential genotoxicity.

BRIEF DESCRIPTION OF THE DRAWINGS

The invention will be further apparent from the following description, with reference to the several figures of the accompanying drawings, which show, by way of example only, one form of detection of damaged DNA. Of the figures.

EXPERIMENTAL

DESCRIPTION OF THE PREFERRED EMBODIMENT

Materials

Figure 1:
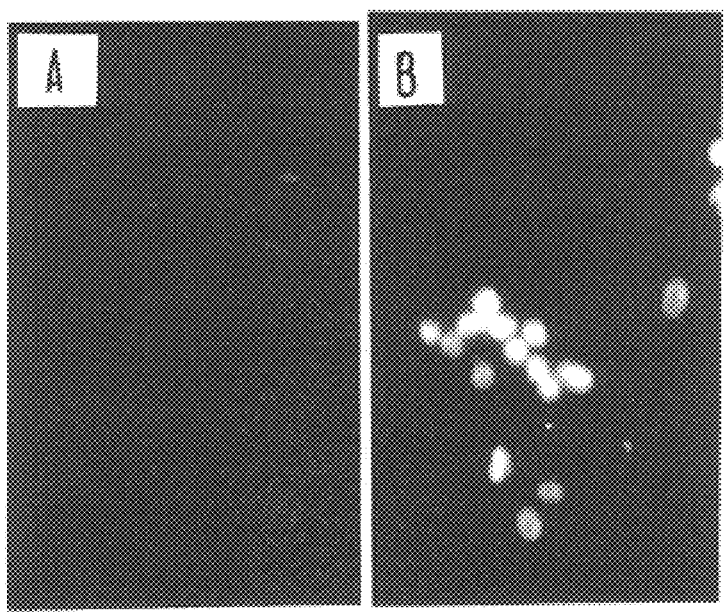
FIG. 1 shows avidin binding to UVA-treated cells. Avidin-FITCS (fluorescein isothiocyanate) bound to the nucleus of IMR 32 cells irradiated with UVA for 10 mins at room temperature. Cells were fixed and permeabilised immediately after irradiation. Antibody binding (not shown) was visualised with avidin-FITCS. In the absence of any primary antibody avidin bound to nuclear material in irradiated cells (B). There was no binding to sham-irradiated controls (A).

IMR 32 neuroblastoma cells (passage number 66) were from the European Collection of Animal Cell Cultures (ECACC) (Porton Down, Salisbury).

Avidin-FITCS conjugate was from Sigma (A 2050), as was monoclonal, goat anti-biotin-FITCS conjugate antibody (clone number BN-34) (F4024).

Streptavidin-horse radish peroxidase conjugate was from Biotrin (Dublin, Eire)

The UVA (366 nm) lamp was from Knight Optical Technologies as was the Optical Radiometer.

CENTRICON microconcentrators were from Amicon (Stonehouse, U.K.)

DNA bases-synthesis of 8-oxodeoxyguanosine was made in the laboratory according to the Udenfriend system (Kasai and Nishimura, 1984, Mutation Research, 12: 2137–2145) and its purity checked by electrospray mass spectrometry.

Molecular Modelling

Three-dimensional models of the oxidised bases and biotin were generated using the DESKTOP MOLECULAR MODELLING (Oxford University Press, 1994) program, Structures were minimised using this program.

Capillary Electrophoresis Analysis of Binding

Capillary electrophoresis was used to study the ability of avidin to bind to both 8-oxoguanine (Sigma) and biotin (Sigma) (Poon et al., 1995 supra). Capillary electrophoresis was performed using a Beckman P/ACE (RTM) 2200 (High Wycombe, U.K.) controlled by accompanying System Gold (RTM) software. All analyses were carried out using an untreated fused silica capillary of 57 cm total length and 75 μm internal diameter. Biotin and 8-oxoguanine were analysed using free zone capillary electrophoresis. Avidin was added to either 8-oxoguanine (100 μM final concentration) or to a biotin solution (100 μM final concentration) to give theoretical binding ratios of between 84% and 0%. The resulting solutions were passed through a Centricon microconcentrator (C Con 30 and C Con 10 for biotin and 8-oxoguanine solutions respectively) and the concentrate centrifuged at 200 rpm at 4° C. for 20 mins. Samples were then placed on ice until analysed by CE. The electrophoresis solution was 10 mM sodium tetraborate (pH 9.3) filtered through a 0.45 μm filter. Samples were loaded using positive pressure (nominal 0.5 psi) for 5 seconds at 25° C. The run time was 10 minutes under an applied voltage of 30 kV with a rise time of 0.17 minutes (approx. 10.2 seconds). Detection was by absorbence at 200 nm and comparison with known standards. Concentration of each compound was estimated from peak height.

Preparation of Oxidised DNA

Treatment of DNA with methylene blue leads to the oxidation of deoxyguanosine residues to 8-oxodeoxyguanosine. DNA (0.5 mg/ml in water) was incubated in the presence of methylene blue (20 μg/ml final concentration in 0.1 M tris, pH 8.5) in a petri dish on ice shielded from a white light source by 0.5 cm water in an upturned petri dish lid (light source to DNA distance was 3 cm). Irradiation was for 3 hours at which time solid sodium chloride was added to a final concentration of 1 M and the DNA precipitated with ethanol. The DNA was removed and dissolved in de-ionized water. The DNA was re-precipitated and washed twice more to remove any remaining methylene blue.

Enzyme-linked Avidin Binding Assay

Avidin-horse radish peroxidase (avidin-HRP) (Sigma) binding to methylene blue-treated DNA was compared to its binding to untreated DNA. Treatment of DNA with methylene blue leads to the generation of oxidised base products including 8-oxodeoxyguanosine. Competition experiments were carried out to define the specificity of binding of avidin to DNA. Damaged and native DNA bind to ELISA plates and in initial experiments, native and methylene blue-treated double-stranded and single-stranded DNA were bound to ELISA plates (Immuno plate MAXISORP (RTM), Nunc) at 50 μg/ml in PBS (50 μl/well). However since it is difficult to quantify the amount of DNA remaining after the various procedures, Millipore MULTISCREEN (RTM)filtration plates were used in this experiment. Native and methylene blue-treated double-stranded and single-stranded DNA (100 mg/ml in water) was added to appropriate wells (100 g/well) of MULTISCREEN-HV 96-well plates. The base of the wells in these plates is a 0.45 mM, hydrophilic, low protein binding, DURAPORE (RTM) membrane. In these experiments, DNA was fixed with 4% (w/v) paraformaldehyde in PBS (pH 7.4) (100 μl/well) for 5 minutes at room temperature. After fixation the aqueous phase was removed by filtration using a vacuum manifold. Non-specific binding sites were blocked by incubating the DNA in 1.0% (w/v) gelatin in PBS for 5 minutes. The blocking solution was removed by vacuum filtration then the wells washed 3 times with PBS. Avidin-HRP was added to the wells (1:500 in PBS, 50 μl/well) and incubated at 37° C. for 1 h in a humidified chamber. Following washing with PBS 3 times, detection of bound peroxidase-labelled avidin was performed using 50 μl/well of o-phenylenediamine (0.5 mg/ml in 0.05 M phosphate-citrate, pH 5.0, and containing 0.03% w/v sodium perborate as a substitute for $H_2O_2$) as substrate; the reaction was stopped after 20 minutes at room temperature using 2M $H_2O_4$ (25 μl/well) and the product determined spectrophotometrically at 492 nm.

For competition experiments, avidin-HRP was diluted (1:500) directly into solutions of the potential competitors and added directly to the DNA preparations. The potential competitors were prepared in PBS immediately prior to use and pH corrected to 7.4.

Cell Culture

The IMR 32 (passage number 66) cell line was obtained from the European Collection of Animal Cell Cultures (ECACC) (Porton Down, Salisbury). The cells were maintained in a humidified atmosphere of 95% air, 5% $CO_2$ at 37° C. The IMR 32 cell line was routinely maintained in a-minimal essential medium (α-MEM) with 10% (v/v) HIFCS (heat-inactivated foetal calf serum) and 1% (v/v) non-essential amino acids (NEAA). No antibiotics were used at any time.

Stock cultures were maintained sub-confluent in the logarithmic growth phase. Cultures were not passaged more than 15 times before reverting to the frozen stocks. IMR 32 cells were detached for harvesting and passage by shaking in a small volume of fresh medium.

The cells were resuspended in fresh medium by gentle trituration through a 19 gauge needle. To maintain stocks, cells were replated at approximately $2 \times 10^6$ cells/75 cm$^2$ flasks.

Cultures were chemically differentiated before all experiments. For quantification of DNA damage by fluorimetry and measurement of 3-(4,5)-dimethyl-thiazol-2-yl-2,5-diphenyl tetrazolium bromide (MTT) metabolism, cells were plated out in 96-well plates. IMR 32 cells were plated out in 96-well plates at $2 \times 10^5$ cells per well in 200 $\mu$l of medium ($\alpha$-MEM with 5% (v/v) HIFCS and 1% (v/v) non-essential amino acids) with 5'-bromodeoxyuridine ($1 \times 10^{-5}$M) and allowed to differentiate for various time periods (Thomas, S. M. and Anderton, B. H., 1991, Toxic. In Vitro, 5: 173–180). For fluorescence cytochemistry cells were plated out in 8-chamber plastic LABTEK (RTM) slides at $2 \times 10^5$ cells per well in 300 $\mu$l of medium ($\alpha$-MEM with 5% (v/v) HIFCS and 1% (v/v) non-essential amino acids) with 5'-bromodeoxyuridine ($1 \times 10^{-5}$M).

Fluorescent Binding Assay (FBA) for 8-oxodeoxyguanosine

Cultures of IMR 32 cells were grown in 96-well plates as described above and allowed to differentiate. Untreated cultures were fixed and permeabilised as above to provide a substrate to which 8-oxodeoxyguanosine would bind thus permitting FAAs to be performed. Various concentrations of either the normal or the oxidised base were incubated on these plates (100 $\mu$l/well) for 1 hour. The ELISA plates were then washed 3 times with PBS before visualising bound base with either avidin-conjugated FITCS (1:200 in PBS for 1 hour) or with a FITCS-conjugated anti-biotin monoclonal antibody (1:80 in PBS for 1 hour). The level of binding was quantified with a fluorescence plate reader (Denley, Billingshurst, U.K.), excitation 485 nm and emission 535 nm.

Hydrogen Peroxide Treatment

After differentiation, media was carefully aspirated and prewarmed Hanks buffered salt solution (HBSS) added to each well (200 $\mu$l) with or without various concentrations of freshly prepared hydrogen peroxide. The cultures were incubated with hydrogen peroxide for 1 hour after which the HBSS was replaced with fresh media ($\alpha$-MEM with 5% (v/v) HIFCS and 1% (v/v) non-essential amino acids) and allowed to recover for 24 hours under standard incubation conditions before cell death was assessed using the MTT assay and binding of avidin assessed by fluorescence analysis.

UVA Exposure

Differentiated cells were exposed to UVA irradiation with or without preincubation with the lipid-phase antioxidant $\alpha$-tocopherol. The level of UVA irradiation was monitored in each experiment with a radiometer. Antioxidant was added to the existing medium 24 hours prior to irradiation at a final concentration of 200 $\mu$M (stock made up immediately prior to use in ethanol). Control cultures had an equal volume of vehicle (ethanol) added. Medium was removed prior to irradiation and cells washed in HBSS. The cells were irradiated from above at room temperature. Controls were sham irradiated. The cells were fixed as described below.

MTT Assay

The reduction of MTT by mitochondrial succinate dehydrogenase (Mosmann, T., 1983, Immunol Methods 65(1–2): 55–63) is a standard colorimetric, cytotoxicity assay. One hour before each time point, 20 $\mu$l of MTT (5 mg/ml in PBS) was added to each well and cell cultures incubated for 1 hour at 37° C. The medium was carefully aspirated and 100 $\mu$l of isopropanol added to each well to solubilise the formazan product deposited within the viable cells. Absorbence was read at 550 nm on a scanning multiwell spectrophotometer after agitating the plates for 5 minutes to ensure complete dissolution of the formazan product.

Fluorescent Assessment of Avidin Binding

Cells were prefixed by the addition of 2% (w/v) paraformaldehyde (in phosphate buffered saline (PBS) at pH 7.4) for 15 mins after washing the cells with PBS. Cells were washed in warm PBS. Cultures were fixed and permeabilised with ice-cold methanol for 15 minutes, rehydrated in PBS before blocking with PBS containing 10% (w/v) normal goat serum (NGS). The blocking solution was washed off with PBS containing 0.2% (w/v) NGS. DNA damage was visualised with avidin-conjugated fluorescein isothiocyanate (FITCS) (1:200 in PBS for 1 hour) or with a FITCS-conjugated anti-biotin monoclonal antibody (1:80 in PBS for 1 hour) for either fluorescence microscopy or for quantitative assessment with a fluorescence plate reader (Denley, Billingshurst, U.K.).

Inhibition of Avidin Binding

The ability of modified DNA bases and biotin to prevent binding of avidin to hydrogen peroxide treated cells was studied. 100 $\mu$M solutions of biotin, guanine and 8-oxodeoxyguanosine were prepared in PBS (pH 7.4) immediately prior to use. Avidin-FITCS (Sigma) was added (1:100) to the potential competitors and preincubated in the dark at room temperature for 1 hour. The control, PBS in the absence of competitor, was treated in parallel. The solutions were centrifuged at 10,000 g in a microfuge for 5 mins (room temperature) and the supernatant used for binding experiments. Fixed cells were incubated with the solutions for 1 hour in the dark at room temperature. The slides were washed three times in PBS before coverslips were mounted on the slides using VECTORSHIELD (RTM) (Vector Laboratories, Peterborough, U.K.), a glycerol-based anti-bleaching mountant.

Pathological Sections

Flash frozen tissue sections were thawed at room temperature for 15 minutes then fixed by the addition of 4% (w/v) paraformaldehyde (in phosphate buffered saline (PBS) at pH 7.4) with 0.5% glutaraldehyde on ice for 5 mins, and washed in PBS then saline. The samples were dehydrated through alcohol then endogenous peroxidases blocked by incubation in methanol with 0.3% hydrogen peroxide for 15 minutes. The samples were rehydrated and washed in PBS. Avidin binding was visualised with avidin-conjugated fluorescein isothiocyanate (FITCS) (1:200 in PBS) for 1 hour. Sections were washed extensively before coverslips were mounted on the sections using VECTORSHIELD (Vector Laboratories, Peterborough, U.K.), a glycerol-based anti-bleaching mountant, prior to microscopy.

Statistical Analysis

Data were analysed using the STATGRAPHICS V. 5.0 program (STSC Inc., M.A., U.S.A.). Data was checked for normal or non-parametric distribution by using probability plots, prior to analysis. Analysis of variance (ANOVA) procedures and Scheffe multiple range tests at the 95% confidence level were used to assess effects on normally distributed data. Students t-tests at the 95% confidence level were used to compare two samples.

Results

The initial observation was that, very surprisingly, avidin-conjugates bound to DNA in the absence of any antibody in UVA-treated cells. Binding of avidin-FITCS to nuclei of UVA-treated cells was observed (FIG. 1B), with no binding to nuclei of sham irradiated cells (FIG. 1A)

Figure 2:
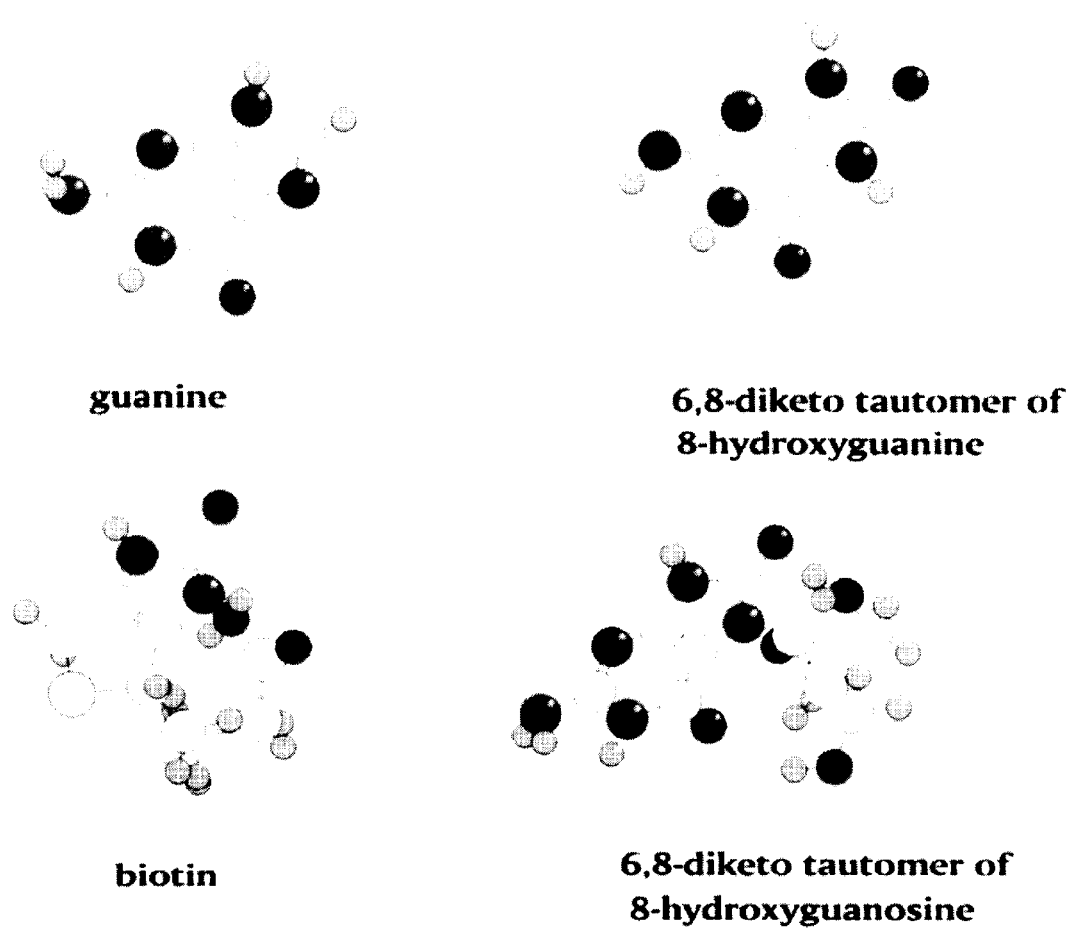
FIG. 2 shows optimised structures of biotin and 8-oxoguanine. Optimised structures of the most common tautomeric form of guanine, the 6,8-diketo tautomers of 8-hydroxyguanine and 8-oxodeoxyguanosine, and biotin were generated using the DESKTOP MOLECULAR MODELLING program (below).

An investigation of the structural similarities of oxidatively-modified DNA bases with that of the natural ligand, biotin, showed that although there is little similarity between the unmodified base guanine and biotin, the optimised structures of the 6,8-diketo tautomers (Aida, M. and Nishimura, S., 1987, Mutation Research, 192: 83–89) of both 8-oxoguanine and 8-oxodeoxyguanosine share structural similarity with biotin (FIG. 2). The 6,8-diketo tautomers of both 8-oxoguanine, 8-oxodeoxyguanosine both possess an imidazilidone group in common with biotin, although the deoxyribose group is attached to $N^3$ of the imidazilidone of 8-oxodeoxyguanosine. Biotin possesses a valeric acid group on the $C^2$ of the ureido group. The two rings of biotin are fused in the cis-configuration and the valeric acid side chain is cis with respect to the imidazilidone ring (Green, N. M., 1972, Adv. Protein Chem., 29: 85–131). Although neither 8-oxoguanine nor 8-oxodeoxyguanosine have a similar alkyl group, the sugar group of 8-oxodeoxyguanosine lies in a similar position with respect to the two ring structures and two oxygen groups within the ribose molecule lie in similar positions to the two oxygens of the carboxyl group of the valeric acid (FIG. 2).

Figure 3:
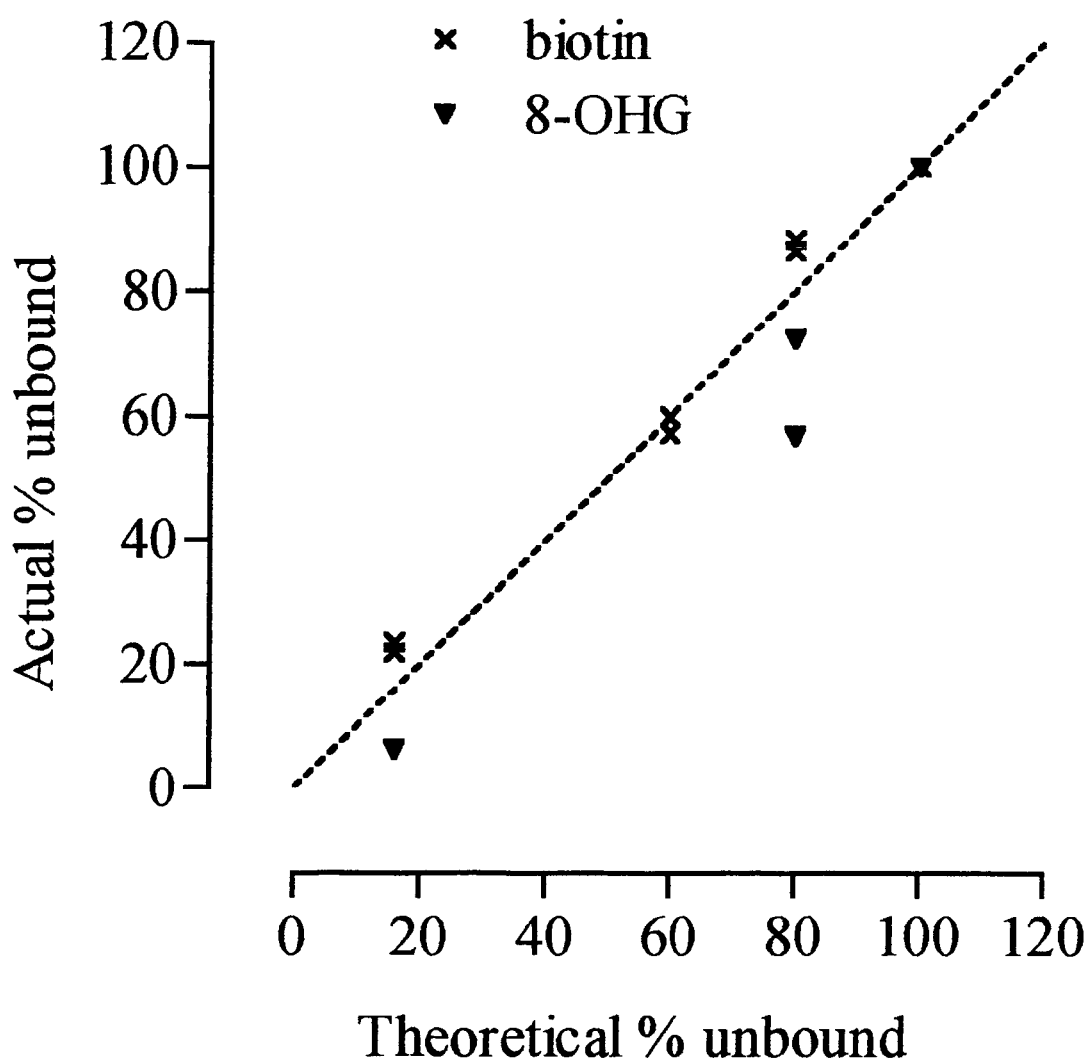
FIG. 3 shows binding of avidin to biotin and 8-oxoguanine as assessed by capillary electrophoresis. After the addition of varying concentrations of avidin to either biotin (A) or 8-oxoguanine (B) (both at 100 $\mu$M), the amount (as a percentage) of unbound biotin or 8-oxoguanine was measured using capillary electrophoresis and plotted against the theoretical amount remaining, assuming a 1:4 ratio of avidin to either biotin or 8-oxoguanine.

The extent of binding of biotin to avidin was demonstrated using a capillary electrophoresis technique monitoring the disappearance of biotin after its incubation with various concentrations of avidin (FIG. 3). Recovery of unbound biotin was very close to the theoretical values expected, assuming a binding ratio of 4 biotin molecules per avidin. A similar technique was applied to monitor the ability of avidin to bind to 8-oxoguanine. After preincubation with avidin the detectable level of 8-oxoguanine was reduced (FIG. 3) apparently with a 1:4 ratio as seen with biotin.

Figure 4:
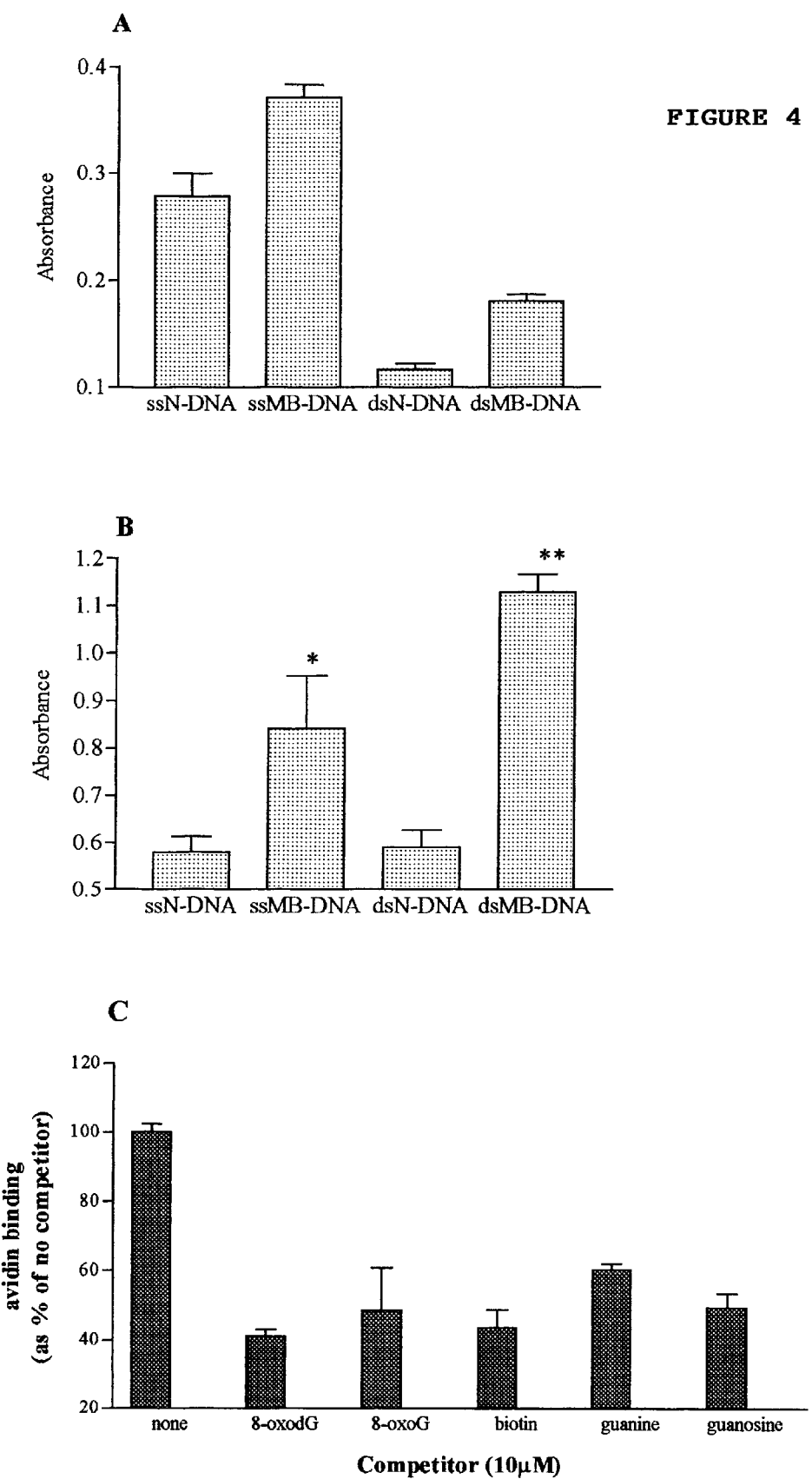
FIG. 4 shows the specificity of avidin for oxidatively-modified DNA. Both single-stranded and double-stranded DNA were treated with methylene blue to generate oxidatively-modified base-damage. The methylene blue and unmodified DNA (100 $\mu$g/ml) were bound to ELISA (enzyme-linked immunosorbent assay) plates (A) (n=8) or to MULTISCREEN (RTM) filtration plates after fixation with 4% (w/v) parafomaldehyde (B) (n=8) and the level of binding of horseradish peroxidase (HRP) -conjugated avidin assessed spectrophotometrically. *=significant at 95% level, **=significant at 99% level with respect to appropriate normal DNA. The ability of several putative competitors (all at 10 $\mu$M) to inhibit binding of avidin to paraformaldehyde-fixed, double-stranded methylene blue-treated DNA was investigated (C). n=8 except for 8-oxodeoxyguanosine and 8 oxoguanine where n=4.

Treatment of DNA with methylene blue leads to oxidative base-damage, specifically generating 8-oxodeoxyguanosine. The affinity of avidin for methylene blue-damaged DNA was investigated using an ELISA-type assay. The level of binding of avidin to both single-stranded and double-stranded methylene blue treated DNA was greater than that seen to normal DNA (FIG. 4A). The level of binding was considerably higher to both normal and methylene blue treated single-stranded DNA than to double-stranded DNA. Fixation of the DNA with paraformaldehyde (4% (w/v)), increased the level of binding of avidin to double-stranded DNA such that there was no longer a significant difference in the level of binding to normal single-stranded and double-stranded DNA (FIG. 4B). The difference in binding of avidin to methylene blue treated DNA when compared to that to normal DNA was highly significant. Although the level of binding of avidin to methylene blue-treated DNA is considerably greater than to normal DNA, there is binding to untreated DNA. However, commercial DNA is processed extensively and even within the experimental procedures employed here the DNA is not protected from oxidative damage. The level of 8-oxoguanine in commercial calf thymus has been determined (not shown) using HPLC; the levels were 0.4 nmol/mg DNA or 3.2 mol/$10^5$ mol guanine. Competition experiments showed that co-incubation with 8-oxodeoxyguanosine (10 µM) produced the greatest inhibition of avidin binding to double-stranded, methylene blue treated DNA (FIG. 4C). Guanine and guanosine also inhibited binding, however the concentration of inhibitor is high (approximately 1000 fold) with respect to the concentration of avidin (approximately $10^{-8}$M).

Figure 5:
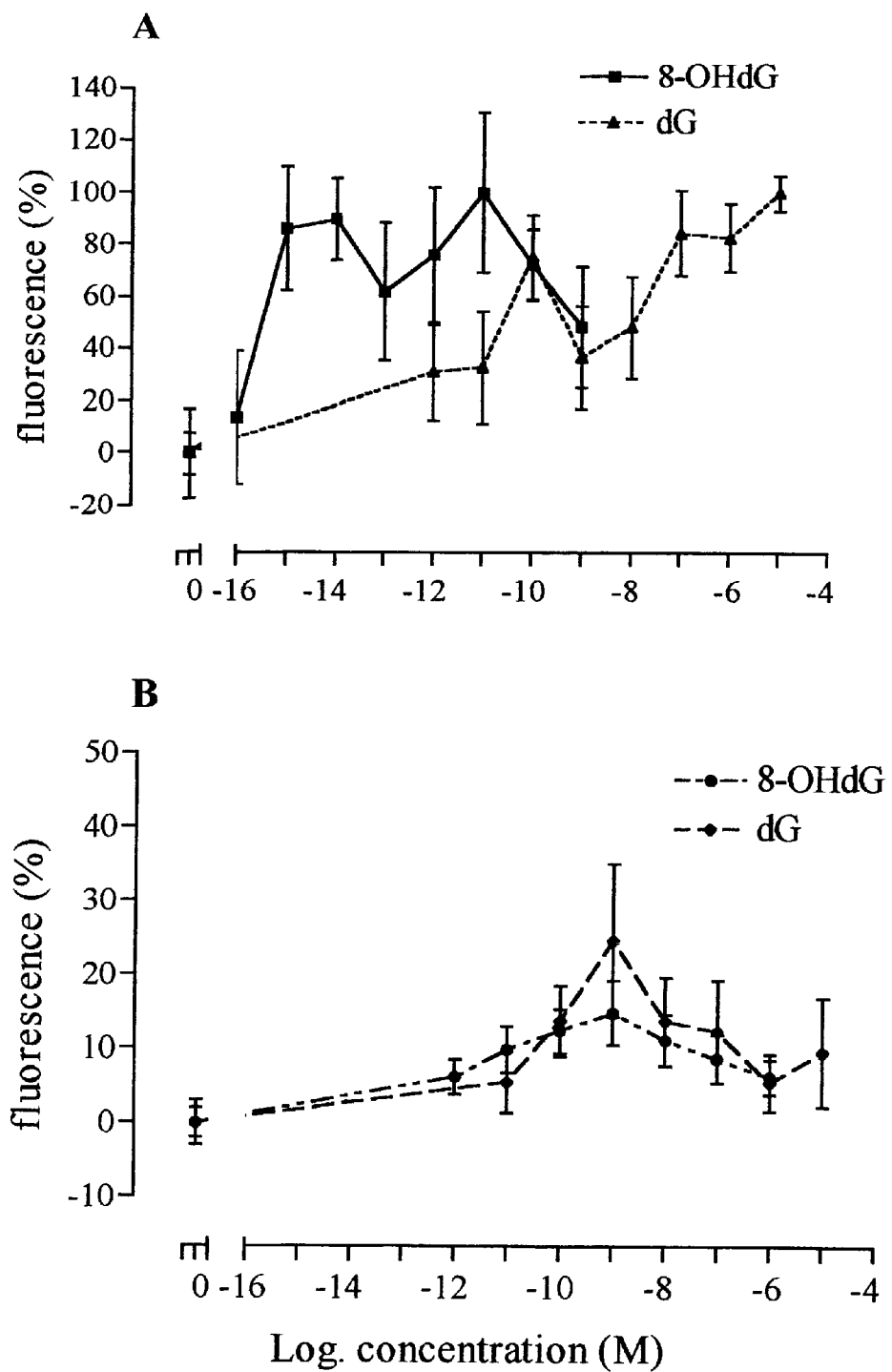
FIG. 5 shows binding of avidin to 8-oxodeoxyguanosine and its unmodified deoxynucleoside analogue. The binding of FITCS-conjugated avidin for 8-oxodeoxyguanosine and deoxyguanosine (A) were assessed by the level of binding seen to different concentrations of the base bound to a substratum of fixed cells. Data are expressed as a percentage of the difference between the maximum and minimum levels of binding (A). There was no statistical difference between the maximum and minimum values for avidin binding to either 8-OHdG (8-oxodeoxyguanosine) or dG (deoxyguanosine). The binding of a FITCS-conjugated monoclonal antibody to biotin for 8-oxodeoxyguanosine and deoxyguanosine (B) were compared to that of avidin by the level of binding seen to different concentrations of the base bound to a substratum of fixed cells. Data are expressed as a percentage of the maximum binding seen with avidin-FITCS. Values are means±standard error of the mean (SEM) where n=8. The data presented are of a representative experiment.
Figure 6:
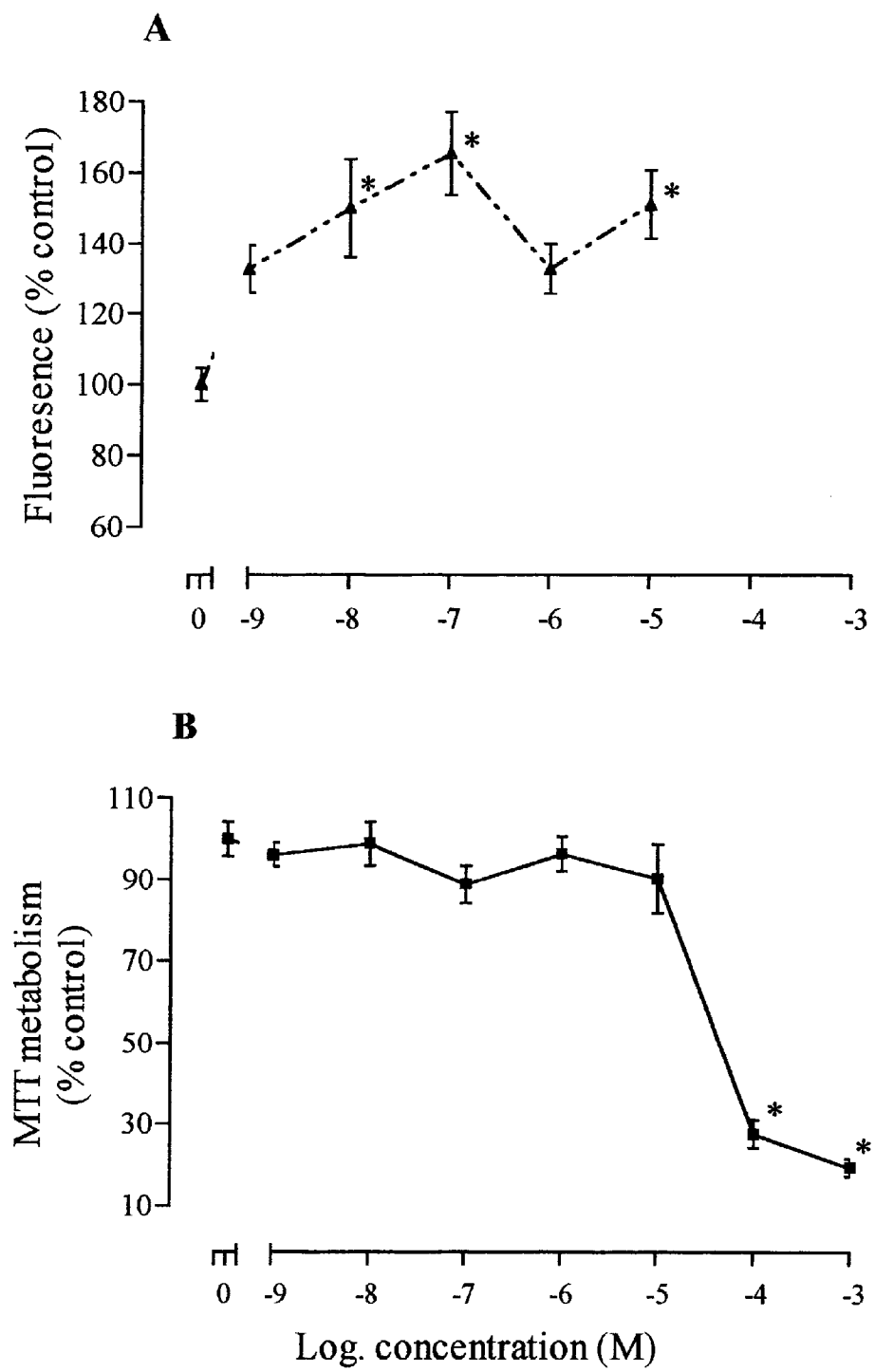
FIG. 6 shows avidin binding to IMR 32 cells treated with hydrogen peroxide. After exposure to various concentrations of hydrogen peroxide in HBSS (Hanks buffered salt solution) for 1 hour, fresh complete medium was added to IMR 32 neuroblastoma cultures and the cultures incubated for 24 hours before assessing the level of binding of avidin using FITCS-conjugated avidin (A). Cytotoxicity was assessed using the MTT (3-(4,5)-dimethyl-thiazol-2-yl-2,5-diphenyl tetrazolium bromide) assay (B). Values are means±standard error of the mean (SEM) where n=8. *=significantly different at the 95% confidence level from that group containing the control value using ANOVA (analysis of variance) procedures and Scheffe multiple range tests. The data presented are of a representative experiment.
Figure 7:
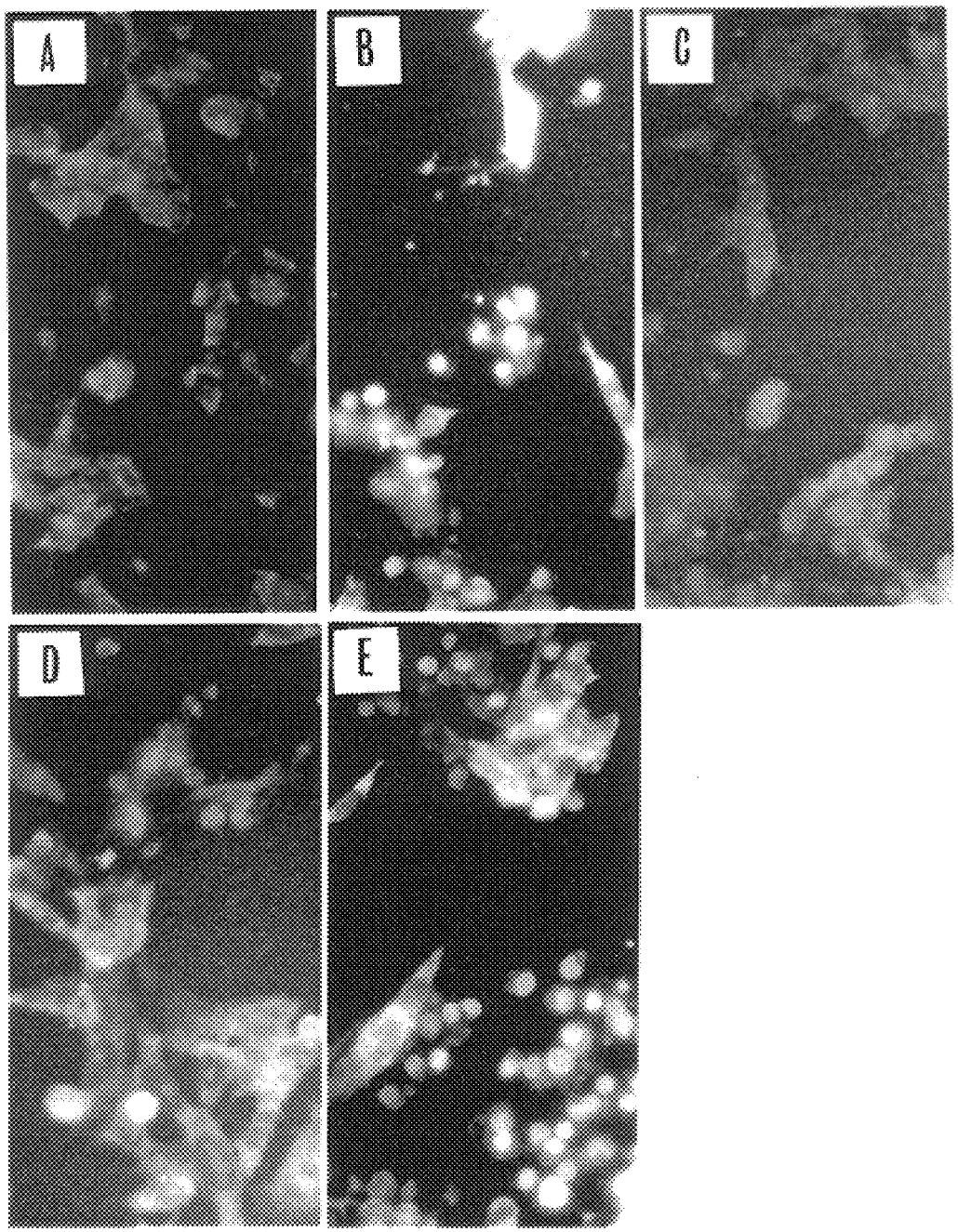
FIG. 7 shows nuclear location of avidin binding in IMR 32 cells treated with hydrogen peroxide. The location of the binding of avidin immediately after exposure of INR 32 cells to HBSS with (A) or without (B) hydrogen peroxide (100 $\mu$M) for 1 hour is shown in photomicrographs (×200) of the cells. The ability of biotin (C), 8-oxodeoxyguanosine (D) and guanine (E) (all at 100 $\mu$M) to inhibit avidin binding was also investigated.

The binding of avidin and a monoclonal antibody to biotin was investigated using different concentrations of 8-oxodeoxyguanosine or deoxyguanosine bound to a substratum of fixed cellular material. Avidin binding reached a maximum at $10^{-15}$ M 8-oxodeoxyguanosine after which concentration, binding remained at approximately the same level (FIG. 5A). In contrast binding to deoxyguanosine increased with increasing concentration, reaching a maximum at $10^{-6}$M deoxyguanosine (FIG. 5B). The 0% and 100% values obtained in these experiments were not statistically different. The monoclonal antibody to biotin did not appear to have the same degree of specificity as avidin, binding to both 8-oxodeoxyguanosine and deoxyguanosine with a maximum at $10^{-9}$M, although it was still able to clearly distinguish damaged DNA from undamaged DNA (FIG. 5C and D). The level of binding of the antibody was considerably lower than that of avidin at the same concentration of deoxynucleoside in the same experiment. Exposure of IMR 32 cultures (differentiated for 24 hours) to hydrogen peroxide for 1 hour lead to a highly significant increase in binding of avidin-FITCS with respect to hydrogen peroxide concentration p=0.0026 using ANOVA). With 10 nM hydrogen peroxide (FIG. 6A) the level of avidin binding was statistically different from the group that contained the control. An inherent level of fluorescence observed with control cultures is attributable to a low level of inherent binding of the avidin-FITCS, observable by microscopical analysis, and to autofluorescence of the cellular material. The level of binding plateaued at 100 nM hydrogen peroxide. In contrast, overt cell death 24 hours after the initial exposure was only seen at concentrations of hydrogen peroxide of 100 µM and greater (FIG. 6B). The binding of the avidin-FITCS was primarily located in the nucleus of cultures (FIG. 7B) whereas no nuclear binding was observable in cells not treated with hydrogen peroxide (FIG. 7A).

Inhibition studies were carried out in order to determine whether the avidin-FITCS binding could be prevented by preincubation with biotin, to establish that binding was specific and involved the biotin binding site and also with 8-oxodeoxyguanosine as a competitor (FIG. 7A–E). In the first instance, the avidin conjugate was preincubated with various potential competitors prior to incubation with cells that had been exposed to hydrogen peroxide. As was expected preincubation with 10 µM biotin prevented binding to the treated cells (FIG. 7C). 8-oxodeoxyguanosine also inhibited binding (FIG. 7D), whereas guanine did not (all at 100 µM) (FIG. 7E) prevent binding. These findings imply that the biotin binding site is involved in the binding to the nuclear DNA. Direct competition experiments, where the competitors and the avidin-conjugate where added simultaneously to the treated cells showed the same pattern of inhibition of binding.

Figure 8:
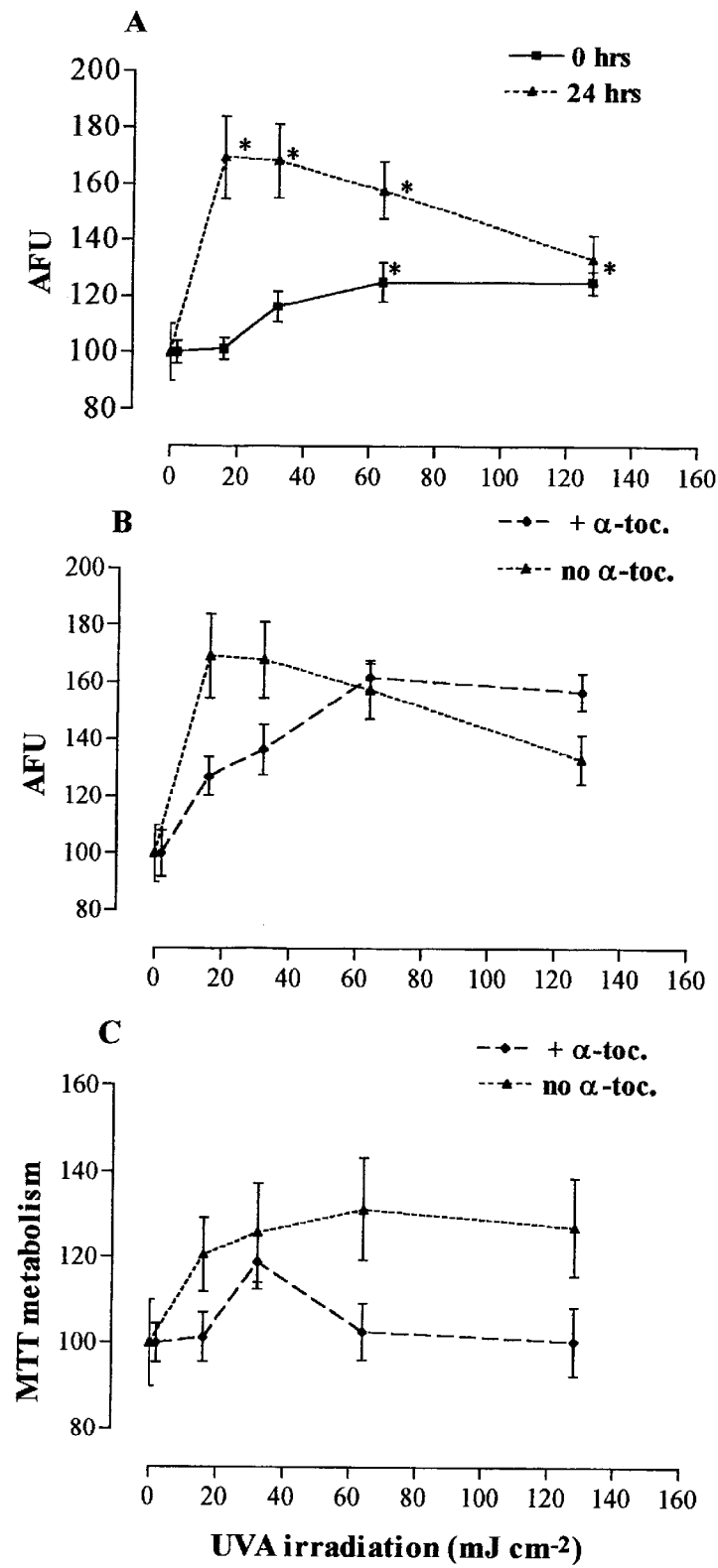
FIG. 8 shows avidin binding to UVA irradiated IMR 32 cells. Differentiated IMR 32 cells were irradiated with UVA (maximum 0.2 mJ cm$^{-2}$) and binding of avidin-FITCS assessed either immediately after irradiation or 24 hours after irradiation (A). The effect of preincubation with α-tocopherol on avidin binding to cells 24 hours post-irradiation (B). Viability of cells 24 hours post-irradiation was assessed using the MTT assay (C). Values are means±standard error of the mean (SEM) where n=8. *=significantly different at the 95% confidence level from that group containing the control value using ANOVA procedures and Scheffe multiple range tests. The data presented are of a representative experiment.
Figure 9:
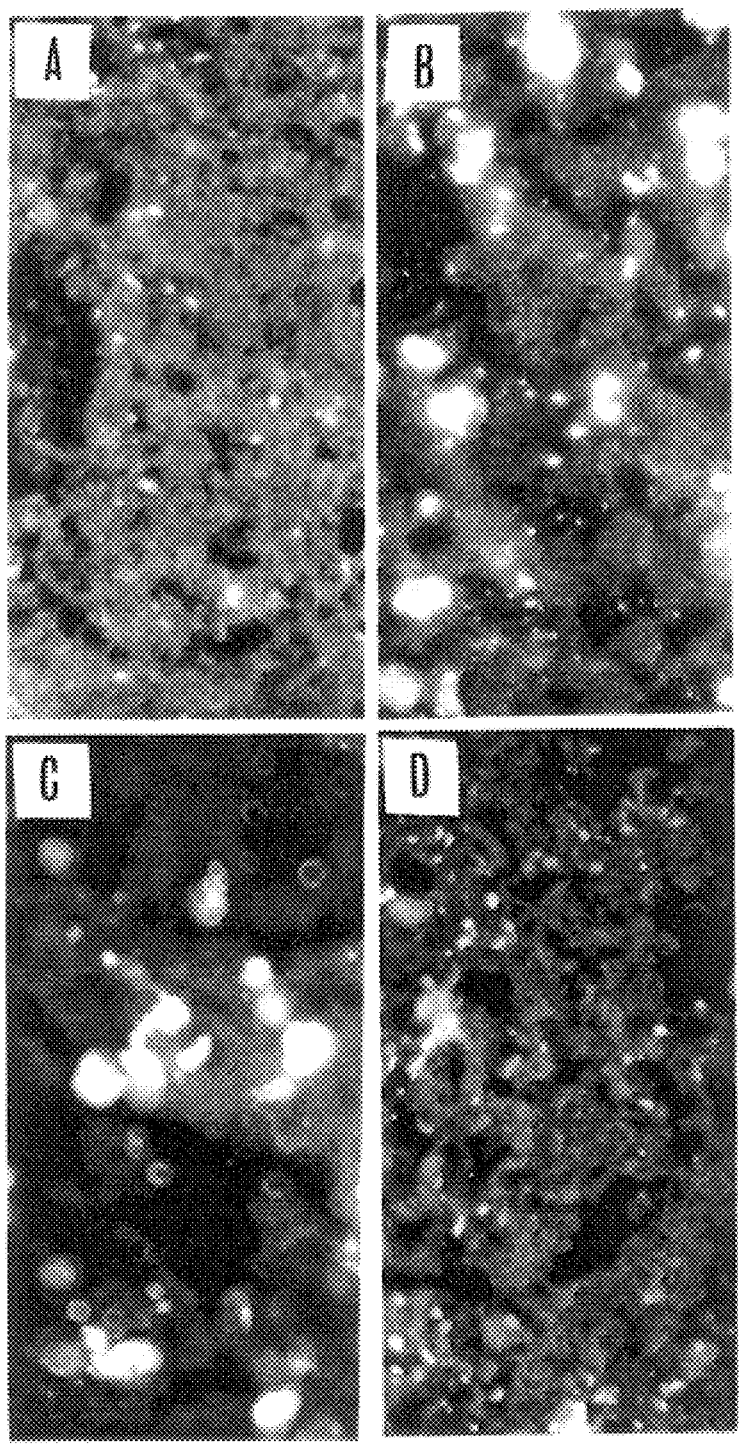
FIG. 9 shows avidin binding to motor cortex sections from patients with motor neurone disease (MND). Frozen sections (12 μM) of motor cortex were fixed and permeabilised with paraformaldehyde (2% w/v in PBS (phosphate buffered saline)) then ice cold methanol. A: male, 65 years control; B: female, 69 years MND: female, 75 years MND; D: female 74 years control. Avidin-FITCS was seen to bind directly to MND) cortex sections.

To further establish that the binding of avidin-conjugates to DNA in cultured cells insulted by free radical generating systems is dependent on oxidatively-mediated events, the ability of an antioxidant to prevent this binding was investigated. Differentiated IMR 32 cells were UVA irradiated to initiate DNA damage. Binding of avidin to the cells was evident immediately after UVA irradiation (p=0.008 using ANOVA), and binding to cells irradiated at 64 mJ cm$^{-2}$ and greater was statistically different from the group containing the control. 24 hours post-irradiation, the level of binding was considerably greater (p=0.0005 using ANOVA) and in cells that had been irradiated with only 16 mJ cm$^{-2}$ the effect was significantly different from control (FIG. 8A). Preincubation with α-tocopherol (200 µM) reduced the level of avidin binding (FIG. 8B) with short periods of irradiation but was not effective in reducing binding after longer periods of irradiation. Multiple range ANOVA procedures showed that α-tocopherol significantly (p=0.003) reduced the binding of avidin over the range of irradiation times studied. Viability of the cultures after irradiation was assessed using the MTT assay to establish that binding of avidin was not associated with immediate cell death (FIG. 8C). There was no statistically significant change in viability. An increase in MTT metabolism was seen although this was prevented by α-tocopherol pre-incubation.

The binding of avidin-FITCS to post-mortem sections of neural tissue from patients who died of neurodegenerative disease was compared to that of age matched controls (FIG. 9A–D). Although there was evidence of some binding in the aged controls (FIG. A and D), the level of binding was much higher in those of the MND (FIG. B and C) patients. The study of other bodily tissue samples may be readily achieved using the same or similar methods. The use of human pathological tissue demonstrates that the technique is also applicable to tissue, as well as in vitro systems.

Discussion

Hence avidin, streptavidin and antibody specific to biotin bind specifically to damaged DNA, the prior art not teaching this (see for example Wood, G. S. and Warnke, R., 1981, J. Histochem. Cytochem., 29: 1196–1204)

Binding studies in a purely chemical system suggest that the binding of 8-oxoguanine to avidin is extremely rapid, since minimal preincubation was required to see a reduction in unbound compound. The binding ratio was comparable to the theoretical ratio of 4:1 with respect to avidin, and is consistent with the existence of 4 binding sites on each avidin molecule and with the suggestion that the binding site of avidin is involved in the binding of 8-oxoguanine.

The binding of avidin to free radical-damaged DNA is not dependent on the conjugate nor the end-point method of detection. The inhibition studies also suggest that binding of avidin to DNA is specific, and dependent upon the biotin binding site of avidin since biotin inhibits binding of avidin. 8-oxodeoxyguanosine can also block binding and therefore this suggests that this compound also binds to the biotin binding site. Although guanine and guanosine also inhibit avidin binding, this is only at high concentrations. Therefore, these data strongly suggest that the binding is mediated by the binding site of avidin. The sensitivity of avidin as a detection system for 8-oxodeoxyguanosine was also assessed. Assuming 100% binding of 8-oxodeoxyguanosine to the substratum, this suggests that the theoretical (and conservative) sensitivity of avidin binding to oxidised DNA allows detection of $10^4$ molecules of 8-oxodeoxyguanosine.

The structure recognised by avidin on the DNA appears to be generated by an oxidative free-radical mechanism, since there is a reduction in binding of avidin to UVA irradiated cells that have been pre-incubated with α-tocopherol. The level of binding of avidin to cells increases in an insult-dependent manner, whether this is mediated by UVA irradiation or incubation with hydrogen peroxide, both established means of generating oxidatively-mediated DNA damage, including the generation of 8-oxodeoxyguanosine. Similar binding of avidin to free radical-damaged cells has also been observed with other cell lines, including other neuroblastoma cell lines and 3T3 fibroblast cells.

Avidin-conjugates appear to have similar affinities for 8-oxodeoxyguanosine, 8-oxoguanine and biotin. Avidin has been used to demonstrate damage to DNA in both fixed cellular material from in vitro culture experiments and also in fixed pathological sections. The application of this technique potentially covers a wide range of usages. DNA damage is currently being intensely researched and the methodology used is both expensive and time consuming. Although 8-oxodeoxyguanosine is only one of a range of oxidative DNA damage products (Dizdaroglu, M., 1994, Methods Enzymol., 234: 3–16), it has been suggested that it is an acceptable biomarker of oxidative DNA damage. The direct identification of 8-oxodeoxyguanosine in pathological specimens without the pre-requisite for extraction or purification prior to identification makes it an attractive and acceptable biomarker.

What is claimed is:

1. A method for detecting nucleic acid base damage comprising the steps of:

a) reacting a nucleic acid base-containing sample with an molecule comprising a molecule which binds specifically to biotin and to at least one of 8-oxoguanine, 8-oxodeoxyguanosine, 8-oxoadenine and 8-oxodeoxyadenosine;

b) detecting any binding reaction between the sample and the molecule; and c) correlating detection of the sample-molecule binding reaction with the existence and quantity of damaged nucleic acid bases.

2. A method for detection according to claim 1 in which the said molecule binds to oxidative base-damaged nucleic acids.

3. A method for detection according to claim 1, in which the said molecule binds to said damaged DNA bases.

4. A method for detection according to claim 1, in which the said molecule binds to said damaged RNA bases.

5. A method for detection according to claim 1, in which the said molecule binds to damaged nucleic acid bases of a single-stranded nucleic acid molecule.

6. A method for detection according to claim 1, in which the said molecule binds to damaged nucleic acid bases of a double-stranded nucleic acid molecule.

7. A method for detection according to claim 1, the damaged nucleic acid bases being damaged nuclear DNA bases.

8. A method for detection according to any one of claim 1, the damaged nucleic acid bases being damaged mitochondrial DNA bases.

9. A method for detection according to claim 1 in which it is a method diagnosis of the human or animal body.

10. The method according to claim 1, in which the molecule is selected from any one of the group consisting of avidin and streptavidin.

11. The method according to claim 10, in which the molecule is a fragment or analogue of avidin or streptavidin.

12. The method according to claim 1, in which the molecule comprises an antibody or an antigen binding fragment thereof.

13. The method according to claim 1, wherein the molecule further comprises a monoclonal antibody.

14. The method according to claim 13, wherein the monoclonal antibody comprises the BN-34 antibody supplied by Sigma (F 4024).

* * * * *